United States Patent [19]
Mornhinweg et al.

[11] Patent Number: 5,191,889
[45] Date of Patent: Mar. 9, 1993

[54] TRANSDUCER HEAD FOR A MEDICAL INSTRUMENT AND METHOD OF USE

[75] Inventors: Markus Mornhinweg, Ulm; Fritz Stepper, Boeblingen, both of Fed. Rep. of Germany

[73] Assignee: Hewlett-Packard Company, Palo Alto, Calif.

[21] Appl. No.: 680,563

[22] Filed: Apr. 4, 1991

[30] Foreign Application Priority Data

Apr. 27, 1990 [DE] Fed. Rep. of Germany ... 9004824[U]

[51] Int. Cl.$^5$ .............................................. A61B 8/02
[52] U.S. Cl. .................. 128/662.04; 128/644
[58] Field of Search ............. 128/644, 662.03, 662.04, 128/671–672, 690, 698, 773–775, 782, 677, 680, 685–686, 715, 720–721, 802, 384–385; 24/170, 191, 163 K; D10/31, 32

[56] References Cited

U.S. PATENT DOCUMENTS

| 448,128 | 3/1891 | Crisp et al. ............................ 128/385 |
| 459,681 | 9/1891 | Dorenwend ........................... 128/388 |
| 566,227 | 8/1896 | Rosenkranz ............................ 24/191 |
| 3,780,725 | 12/1973 | Goldberg ........................ 128/662.04 |
| 4,129,125 | 12/1978 | Lester et al. .......................... 128/671 |
| 4,640,295 | 2/1987 | Isaacson ................................ 128/775 |
| 4,726,625 | 2/1988 | Bougher ................................ 24/170 |

FOREIGN PATENT DOCUMENTS

| 0159434 | 10/1985 | European Pat. Off. . |
| 0300069 | 1/1989 | European Pat. Off. . |
| 2343709A1 | 8/1973 | Fed. Rep. of Germany . |
| 2826391A1 | 6/1978 | Fed. Rep. of Germany . |
| 2925699A1 | 6/1979 | Fed. Rep. of Germany . |
| 3444635A1 | 12/1984 | Fed. Rep. of Germany . |

Primary Examiner—Lee S. Cohen
Assistant Examiner—Jeffrey R. Jastrzab

[57] ABSTRACT

A transducer head for a medical instrument (e.g., a cardiotocographic instrument for performing extra-uterine ultrasonic supervision of the fetal heart function) having a housing adapted to be fixed, with the aid of a fastening device and abdominal belt, in a specific position relative to and in contact with the abdomen of a patient is characterized in that the fastening device comprises a bow pivotally attached to the housing and adapted to be locked relative to the housing in a position wherein the belt extends across the housing between the housing and the bow.

8 Claims, 2 Drawing Sheets

TRANSDUCER HEAD FOR A MEDICAL INSTRUMENT AND METHOD OF USE

FIELD OF THE INVENTION

The present invention generally relates to transducer heads for medical instruments. The invention more particularly relates to a cardiotocographic instrument for performing extra-uterine ultrasonic supervision of the fetal heart function and uterine contractions during pregnancy or parturition, and still more particularly relates to a method and apparatus for holding a medical instrument in a predetermined position relative to and in contact with a patient; e.g., in contact with a pregnant woman's abdomen.

BACKGROUND OF THE INVENTION

The present invention especially relates to transducer heads or sensor heads for cardiography, tocography of cardiolocography for detecting the heart function or frequency of a fetus in the womb or the uterine activity referred to as toco, or for simultaneously detecting both parameters. The heart function or frequency of the fetus in the womb is normally detected by an ultrasonic transducer head externally attached to the pregnant woman's abdomen and fixed in position by means of an abdominal belt. The signals emitted by the ultrasonic transducer head and reflected towards the transducer head by the fetus are received by piezoelectric crystal transducer elements in the transducer head and filtered in a suitable manner. The ultrasonic transducer head must be secured in position by means of the abdominal belt on the abdomen directly above the fetal heart so as to guarantee a good transmission of ultrasonic signals between the housing and the tissue or vice versa.

Uterine activity can be detected by a transducer head referred to as a "tocodynamometer," the tocodynamometer being fastened to the woman's abdomen directly above the fundus uteri by means of an abdominal belt. Such a transducer operates as a dynamometer for measuring the respective forces applied by the abdominal belt and uterus to a penetrating prod. The prod projects slightly above the flat contacting surface of the housing and is normally connected to one or several strain measuring resistors. The toco transducer head determines the hardness and deformation of the uterus, and serves to detect the contraction frequency, contraction strength (amplitude) and contraction shape of the uterus. In addition, combined transducer heads for simultaneous ultrasonic supervision of fetal heart function and uterine activity (toco) are referred to as "cardiolocographic" transducer heads.

With regard to the fundamental function and construction of the above-described transducer heads, reference is made to prepublished EP-A1-300069, the disclosure of which is the basis for the disclosure of the present application. The known transducer heads typically have a flat, cylindrical housing with a substantially circular contacting surface which is brought into contact with the patient's abdomen. The housing can be slipped under the abdominal belt in a secured position, and can be fastened to the belt by bringing a button, which is provided on the side of the housing facing away from the abdomen, into engagement with a complementary buttonhole provided in the belt. If the patient changes her position, or if the belt slips relative to the abdomen, tensile forces acting transversely to the direction of the belt may produce (via the button on the housing) a tilting movement which impairs the contact between the contacting surface of the housing and the patient's abdomen; thus, it follows that when excessively high forces act on the head transversely to the direction of the belt, the signal to be measured will be impaired or, even worse, lost.

An additional problem of the known transducer head is that when the abdominal belt has been closed by means of the button it is impossible to displace the transducer head. If repositioning the transducer head is required, it will either be necessary to open the abdominal belt and close it again after the transducer head has been repositioned, or pull the whole abdominal belt and transducer head through below the patient's back, which will cause unreasonable strain to a pregnant woman.

Another problem arising in the handling of the known transducer head is that, during positioning of the transducer head and the subsequent belt closing operation, the person carrying out the treatment must use both hands for holding and attaching the transducer head and the belt. Still another disadvantage of the known transducer head is that the transducer head can only be secured in position with a belt that is specifically adapted to the transducer head and provided with adequate buttonholes.

EP-A2-0159434 discloses a clip-shaped electrode for use in the field of electrocardiography. The clip-shaped electrode has a structural design of such a nature that it encompasses the patient's extremities and brings an electrode into spring-type contact with the extremities. Measurements on the abdomen cannot be carried out by this type of electrode.

DE-A1-3444635 discloses a transducer head for monitoring a patient's heart and circulation, the housing of the transducer head being adapted to be fastened to the patient's thorax by means of a belt. The way in which the housing of the transducer head is secured in position relative to the belt is not explained in detail.

SUMMARY OF THE INVENTION

Taking the disadvantages of the above-described transducer heads as a basis, the primary object of the present invention is to provide a transducer head that can be easily secured in a predefined position relative to the patient in a manner whereby the risk of tilting the transducer head is minimized. A further object of the present invention is to provide a transducer head that can be easily repositioned when necessary. Another object of the present invention is to provide a transducer head that permits the use of a variety of abdominal belts having respective widths up to a maximum width. These and other objects are achieved by the present invention, according to which a transducer head for a medical instrument comprises a housing adapted to be held by a belt in contact with a patient, and fastening means for affixing the housing to the belt. The fastening means comprises a bow adapted to be locked relative to the housing in such a position that the belt extends across the housing on a side of the housing facing away from the patient and rests between the bow and the housing.

A preferred embodiment of a transducer head in accordance with the invention further comprises means for pivotally attaching the bow to the housing so that the bow can be pivoted relative to the housing. In this embodiment the housing is provided with at least one swivel bearing sleeve having an axis extending in the direction of the belt, and the bow forms a bearing pin on at least one of its ends, the bearing pin being supported in the swivel bearing sleeve. The bow, in the locked position, extends from the location where it is pivotally attached to the housing, across the belt, to a location of locking engagement with the housing. In the most preferred embodiment, the bow further comprises at least one bow-locking projection and the housing further comprises at least one locking recess, the bow-locking projection designed to be brought into engagement with the locking recess.

In a still more specific embodiment, the housing further comprises a substantially cylinder-jacketlike circumferential portion, and the bow further comprises at least one pressure-exerting portion which extends from the bearing pin to the bow-locking projection and which, in the locked condition of the bow, extends at a substantially uniform radial distance from the cylinder-jacketlike circumferential portion of the housing. In this embodiment the bow also includes a belt guide edge in the area of the bow-locking projection adapted to contact the belt on a side facing away from the swivel bearing, and means for guiding the belt, including a bent portion adjacent the bearing pin. Most preferably the bow is made of spring steel wire.

The present invention also encompasses a method for holding a medical instrument in a predefined position relative to a patient. The method includes the steps of placing the medical instrument in a housing, affixing the housing to an abdominal belt by locking a bow attached to the housing in such a position that the belt extends across the housing on a side of the housing facing away from the patient and rests between the bow and the housing, and affixing the belt to the patient so that the medical instrument is held in the predefined position.

BRIEF DESCRIPTION OF THE DRAWINGS

A preferred embodiment of a transducer head according to the present invention is explained in detail below with reference to the drawings, in which.

DETAILED DESCRIPTION OF A PREFERRED EMBODIMENT

Figure 1:
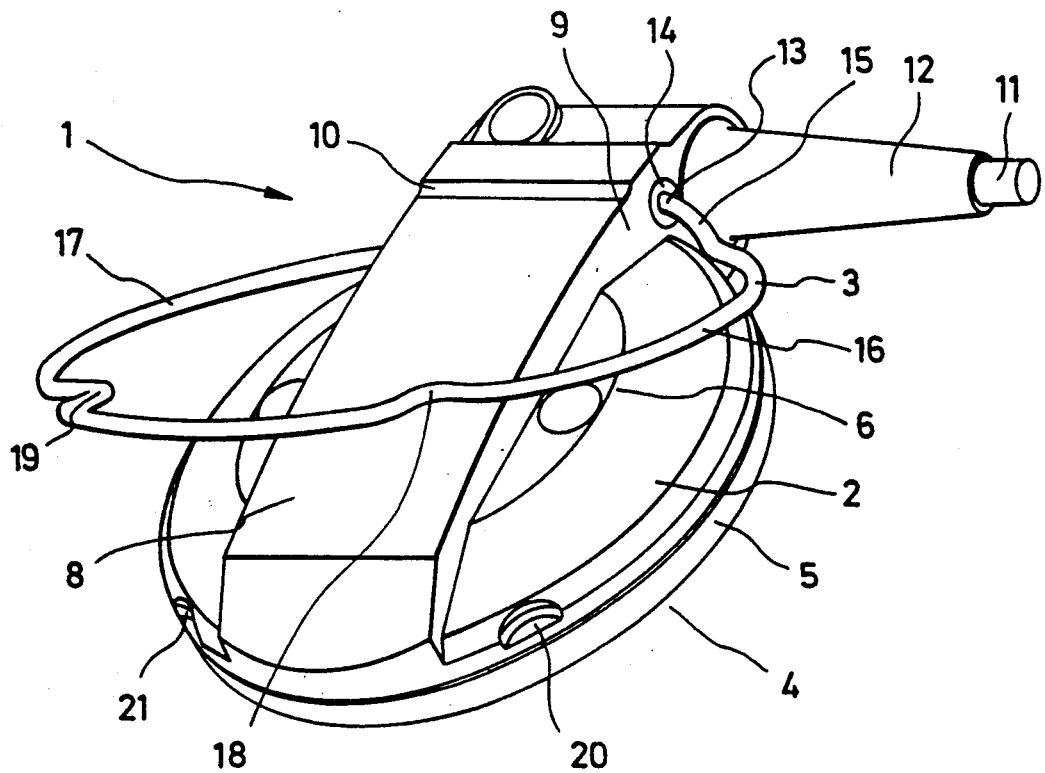
FIG. 1 depicts a perspective view of the transducer head with the bow in an open condition.

As shown in FIG. 1, the transducer head 1 essentially comprises a housing 2 and a bow 3. The housing is provided with a contacting surface 4 with the aid of which the transducer head 1 can be brought into contact with the skin of the patient's abdomen. The semicircular contacting surface 4 merges with a cylinder-jacketlike circumferential portion 5 which in turn merges with an upper side 6 having the shape of a flat truncated cone. A belt support surface 8, which can be flat or slightly spherical, extends diametrically across the upper side 6 at least throughout the width of the belt 7 to be used (see FIG. 2). The belt support surface 8 merges integrally with the upper side 6 of the housing 2 via a belt guide member 9.

Figure 2:
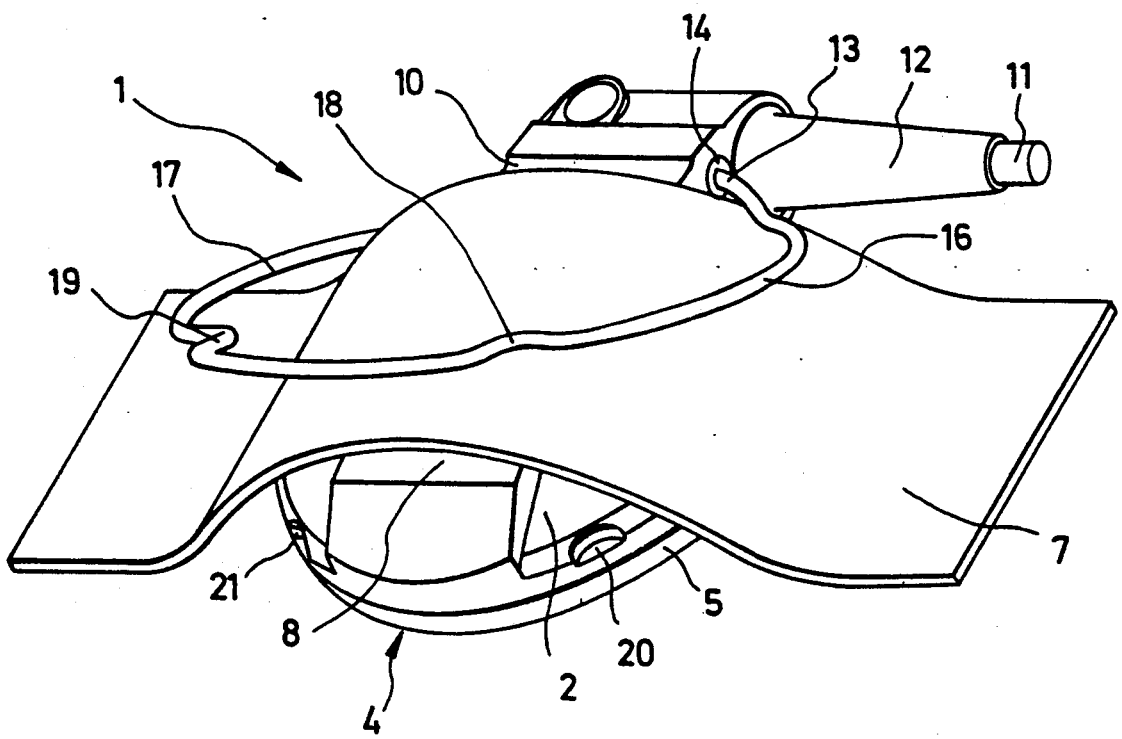
FIG. 2 shows the transducer head of FIG. 1 after a belt has been inserted.

A connection cable 11 for the transducer head 1 is attached to the housing 2 by means of an elastic anti-buckle sleeve 12. The bow 3 merges with bearing pins 13 at both ends of the bow. The housing 2 is provided with two swivel bearing sleeves 14 which are connected to the housing 2 in the area of the belt guide member 9 and which are arranged in such a way that their axes extend in the direction of the belt 7 (FIG. 2). The bearing pins 13 are supported in the swivel bearing sleeves 14.

The bearing pins 13 of the bow are followed by bent portions 15 which extend from the bearing pins 13 and form an angle of approximately 45 degrees towards the contacting surface 4. On the level of the cylinder-jacketlike circumferential portion 5 (when the bow is in the closed position 3 shown in FIG. 3), the bent portions 15 of the bow 3 merge with pressure-exerting portions 16 which, when the bow is closed (FIG. 3), rest against the side of the belt 7 facing away from the abdomen.

Figure 3:
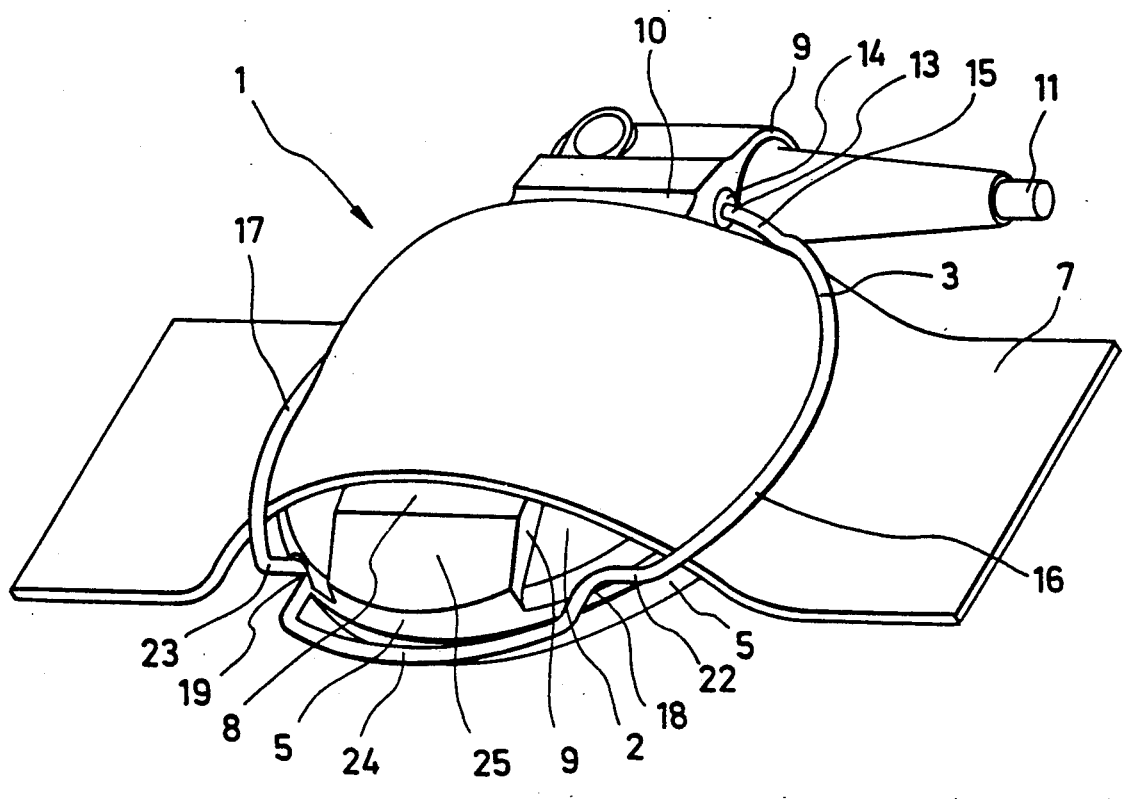
FIG. 3 shows the transducer head of FIGS. 1 and 2 when the bow has been closed over the belt.

The pressure-exerting portions 16, 17 merge with bow-locking projections 18, 19 which, when the bow is closed, lockingly engage locking recesses 20, 21 of the housing 2. As shown in FIG. 3, the bow-locking projections 18, 19 are provided with belt guide edges 22, 23 which are in contact with one side of the belt 7 and which extend essentially parallel to the belt. The belt guide edges 22, 23 produce, together with the belt-guiding bent portions 15 of the bow directly adjacent the bearing pins, a self-aligning effect on the housing 2 when the bow 3 is closed. The bow-locking projections 18, 19 merge with a handle portion 24 extending at an essentially uniform radial distance from the cylinder-jacketlike circumferential portion 5 of the housing 2. The bow 3 consists of an integral body made from spring steel wire.

At the end face of the belt guide member 9 that faces away from the swivel bearing sleeves 14, the housing 2 is provided with a sliding surface 25 that makes it easier to slip the housing 2 of the transducer head 1 below the abdominal belt 7 when the belt has been fastened around the patient's waist. After the housing 2 has been slipped under the abdominal belt 7, the bow 3 is closed, and the bow-locking projections 18, 19 lockingly engage the locking recesses 20, 21. In this condition, the belt extends between the bow 3 and the housing 2 in such a way that, on the one hand, the belt extends across the housing 2 on the side of the housing facing away from the abdomen and, on the other hand, rests against the sides of the pressure-exerting portions 16, 17 of the bow 3 facing the abdomen at both sides of the housing 2. Preferably, the belt 7 is guided only loosely between the bow 3 and the housing 2 so that the transducer head 1 can be displaced in the direction of the belt when the bow is closed.

The structural design of the fastening device reduces the lever arm with which forces transverse to the direction of the belt act on the housing, thus reducing the risk of the transducer being lifted or turned over. The structural design also permits the use of an arbitrary abdominal belt up to a maximum width which is determined by the shape of the bow, independently of the belt closure system. The belt can be attached to the patient independently of the way in which the transducer head is attached to the belt. Thus, in the case of repeated measurements, it is possible to leave the belt attached to the patient; the transducer head being attached to the belt or released from the belt as necessary.

The bowshaped structural design of the fastening device permits repositioning or displacement of the transducer head in the direction of the belt, whereby the measuring accuracy can be increased. In accordance with a further aspect of the invention, the bow is supported such that it can be pivoted relative to the housing; thus the person carrying out the treatment is able to attach the transducer head to the belt with one hand and lock the bow relative to the housing by closing it, thereby securing the transducer head in position relative to the patient's abdomen.

Many variations and modifications of the specific embodiment described above will become apparent upon review of the foregoing specification. Therefore the true scope of the invention is not intended to be limited to the specific embodiment described, but is set forth in the following claims.

What is claimed is:

1. A transducer head for a medical instrument, comprising:
   a housing for a transducer adapted to be held, by a belt, in contact with a patient; and
   fastening means for affixing said housing to said belt, said fastening means comprising a bow adapted to be locked relative to said housing in such a position that said belt extends across said housing on a side of said housing facing away from the patient and rests between said bow and said housing;
   said housing comprising at least one swivel bearing sleeve having an axis extending in a lengthwise direction of the belt; and
   said bow forming a bearing pin on at least one of its ends, said bearing pin being supported in said swivel bearing sleeve.

2. A transducer head according to claim 1, wherein the bow, in the locked position, extends from the location where it is pivotally attached to the housing, across the belt, to a location of locking engagement with the housing.

3. A transducer head according to claim 1 wherein said bow further comprises at least one bow-locking projection and said housing further comprises at least one locking recess, said bow-locking projection adapted to be brought into engagement with said locking recess.

4. A transducer head according to claim 3, wherein said housing further comprises a substantially circular-jacketlike circumferential portion, and said bow further comprises at least one pressure-exerting portion which extends from the bearing pin to the bow-locking projection and which, in the locked condition of the bow, extends at a substantially uniform radial distance from the cylinder-jacketlike circumferential portion of the housing.

5. A transducer head according to claim 1, wherein said bow further comprises:
   at least one bow-locking projection;
   a belt guide edge adapted to contact the belt on a side facing away from said swivel bearing, and
   means for guiding the belt, comprising a bent portion adjacent said bearing pin.

6. A transducer head according to claim 1, wherein said bow is made of spring steel wire.

7. A method for holding a medical instrument in a predefined position relative to a patient, comprising the steps of:
   placing said medical instrument in a housing;
   affixing the housing to a belt by locking a bow attached to said housing in such a position that said belt extends across said housing on a side of said housing facing away from the patient and rests between said bow and said housing; and
   affixing said belt to said patient so that said medical instrument is held in said predefined position.

8. A method for holding a medical instrument in a predefined position relative to a patient, comprising the steps of:
   placing said medical instrument in a housing;
   affixing a belt to said patient; and
   affixing said housing to said belt by locking a bow attached to said housing in such a position that said belt extends across said housing on a side of said housing facing away from said patient and rests between said bow and said housing so that said medical instrument is held in said predefined position.

* * * * *

UNITED STATES PATENT AND TRADEMARK OFFICE
CERTIFICATE OF CORRECTION

PATENT NO. : 5,191,889
DATED : March 9, 1993
INVENTOR(S) : Mornhinweg et al.

It is certified that error appears in the above-identified patent and that said Letters Patent is hereby corrected as shown below:

In column 6, line 12, after "bearing" insert --sleeve--.

Signed and Sealed this

Fifth Day of July, 1994

Attest:

BRUCE LEHMAN

Attesting Officer  Commissioner of Patents and Trademarks